(12) United States Patent
Li et al.

(10) Patent No.: US 10,448,904 B2
(45) Date of Patent: Oct. 22, 2019

(54) DECOMPOSITION METHOD AND APPARATUS BASED ON BASIS MATERIAL COMBINATION

(71) Applicants: TSINGHUA UNIVERSITY, Beijing (CN); NUCTECH COMPANY LIMITED, Beijing (CN)

(72) Inventors: Liang Li, Beijing (CN); Zhiqiang Chen, Beijing (CN); Kejun Kang, Beijing (CN); Ziran Zhao, Beijing (CN); Li Zhang, Beijing (CN); Yuxiang Xing, Beijing (CN); Tiao Zhao, Beijing (CN); Jianmin Li, Beijing (CN); Bicheng Liu, Beijing (CN); Qian Yi, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 16/232,072

(22) Filed: Dec. 26, 2018

(65) Prior Publication Data

US 2019/0192090 A1   Jun. 27, 2019

(30) Foreign Application Priority Data

Dec. 26, 2017   (CN) .......................... 2017 1 1432840

(51) Int. Cl.
*G06K 9/00*     (2006.01)
*A61B 6/03*     (2006.01)
(Continued)

(52) U.S. Cl.
CPC ............ *A61B 6/032* (2013.01); *A61B 6/4266* (2013.01); *A61B 6/488* (2013.01); *G06T 11/005* (2013.01); *G06T 2207/10081* (2013.01)

(58) Field of Classification Search
None
See application file for complete search history.

(56) References Cited

U.S. PATENT DOCUMENTS

| 2007/0237288 | A1* | 10/2007 | Tkaczyk | A61B 6/032 378/5 |
| 2010/0310036 | A1* | 12/2010 | Burleton | A61B 6/405 378/5 |

(Continued)

FOREIGN PATENT DOCUMENTS

GB    2551029 A    12/2017

OTHER PUBLICATIONS

Combined Search and Examination Report dated Jun. 18, 2019 in the corresponding GB application (application No. GB1820957.7).

*Primary Examiner* — Atiba O Fitzpatrick
(74) *Attorney, Agent, or Firm* — Kilpatrick Townsend & Stockton LLP (57) ABSTRACT

The present disclosure provides a decomposition method based on basis material combination. In the present disclosure, a scanned object is divided into a plurality of regions, the basis material combinations used in each of the divided regions are different each other, and the scanned object is re-divided according to the re-determined equivalent atomic number of its each point until the change on decomposition coefficient meets certain conditions. Thereby, a decomposition method based on dynamic basis material combinations is realized, which reduces a decomposition error caused by improper selection of the basis material combination and improves the accuracy of the decomposition and substance identification of the multi-energy CT.

10 Claims, 3 Drawing Sheets

(51) Int. Cl.
*G06T 11/00* (2006.01)
*A61B 6/00* (2006.01)

(56) References Cited

U.S. PATENT DOCUMENTS

| | | |
|---|---|---|
| 2012/0314834 A1* | 12/2012 | Yao .................... G01N 23/046 378/5 |
| 2014/0064587 A1* | 3/2014 | Johnson ................ A61B 6/12 382/131 |
| 2014/0133719 A1 | 5/2014 | Wu et al. |
| 2014/0185901 A1 | 7/2014 | Edic et al. |
| 2015/0161787 A1 | 6/2015 | Li et al. |
| 2016/0202364 A1 | 7/2016 | Wang et al. |

* cited by examiner

DECOMPOSITION METHOD AND APPARATUS BASED ON BASIS MATERIAL COMBINATION

CROSS-REFERENCES TO RELATED APPLICATIONS

The present disclosure is based on and claims priority to China Patent Application No. 201711432840.5 filed on Dec. 26, 2017, the disclosure of which is incorporated by reference herein in its entirety.

FIELD

The present disclosure relates to the field of radiation imaging, and particularly relates to a decomposition method and a decomposition apparatus based on basis material combination.

BACKGROUND

A related X-ray dual-energy CT (Computed Tomography) imaging technique decomposes an attenuation coefficient function of a substance into a linear combination of attenuation coefficient functions of two known basis materials, and coefficients of the linear combination are unknown parameters to be solved. The decomposition of a scanned object uses a fixed set of double basis materials and a corresponding fixed set of attenuation coefficient functions. For example, water and bone can be selected as double basis materials in medical dual-energy CT.

SUMMARY

One aspect of the present disclosure provides a decomposition method based on basis material combination, comprising:

obtaining step for obtaining decomposition coefficients and an equivalent atomic number of each point of a scanned object;

region dividing step for dividing the scanned object into a plurality of regions according to the equivalent atomic number of each point of the scanned object, wherein the basis material combinations used in each of the divided regions are different each other;

decomposing coefficients determining step for, with respect to each of the divided regions, determining decomposition coefficients of each point in the region based on the basis material combination used in the region;

equivalent atomic numbers determining step for, with respect to each of the divided regions, determining equivalent atomic numbers for all points in the divided region based on the determined decomposition coefficients of all points in the divided region and atomic information of all basis materials of the basis material combination used in the divided region, in the case where the change on decomposition coefficient based on the decomposition coefficients of all points in all the divided regions is not less than a preset threshold; and looping step for looping the region dividing step, the decomposing coefficients determining step and equivalent atomic numbers determining step according to the determined equivalent atomic numbers of each point of the scanned object until the change on decomposition coefficient based on the decomposition coefficients of all points in all the divided regions is less than a preset threshold.

In some embodiments of the present disclosure, said region dividing step comprises:

dividing all points located in a same subinterval of a predetermined atomic number relationship chain into one region according to a position of an equivalent atomic number of each point of the scanned object in the atomic number relationship chain, and materials corresponding to the atomic numbers on both endpoints of the subinterval is determined as basis materials constituting a basis material combination of the region.

In some embodiments of the present disclosure, said decomposition coefficients determining step comprising: for each of the divided regions, calculating an integral of the decomposition coefficients of each point in the region along each path through which each ray passes according to projection data of the ray with various energies, an energy spectrum of the region, and attenuation coefficient functions corresponding to the basis material combination of the region;

determining decomposition coefficients of each point in the region according to the integral of the decomposition coefficients of each point in the region along each path through which each ray passes.

In some embodiments of the present disclosure, the energy spectrum of a region is determined according to an energy spectrum of ray source, the decomposition coefficients of all points in other regions outside the region, and the attenuation coefficient functions corresponding to the basis material combinations of the other regions.

In some embodiments of the present disclosure, said equivalent atomic number determining step comprises:

determining an equivalent electron density of each point in a divided region according to a decomposition coefficient of each point in the region and an atomic number and atomic weight of all basis materials of the basis material combination of the region;

determining an equivalent atomic number of each point in the region according to the decomposition coefficient and the equivalent electron density of each point in the region and the atomic number and atomic weight of all basis materials of the basis material combination of the region.

In some embodiments of the present disclosure, the obtaining step obtains the decomposition coefficients and the equivalent atomic numbers of all points of the scanned object according to a preset base material combination.

In some embodiments of the present disclosure, the method further comprising:

in the case where the change on decomposition coefficients is less than the preset threshold, performing substance identification for each of divided region by using the equivalent atomic number of each point in the region.

In some embodiments of the present disclosure, the point comprises a pixel point or a voxel point.

Another aspect of the present disclosure provides a decomposition apparatus based on basis material combination, comprising:

a memory; and a processor coupled to the memory, the processor being configured to perform the method of any one embodiment based on instructions stored in the memory.

One more aspect of the present disclosure provides a computer readable storage medium storing a computer program, the program being executed by a processor to implement the method of any one embodiment.

In the present disclosure, a scanned object is divided into a plurality of regions, the basis material combinations used in each of the divided regions are different each other, and the scanned object is re-divided according to the re-determined equivalent atomic number of its each point until the change on decomposition coefficient meets certain conditions. Thereby, a decomposition method based on dynamic basis material combinations is realized, which reduces a decomposition error caused by improper selection of the basis material combination and improves the accuracy of the decomposition and substance identification of the multi-energy CT. When the range of atomic number variation of the scanned object is large, such as medical CT enhanced imaging (which uses a contrast agent of a material such as iodine), high-energy or multi-energy CT imaging (such as security, air box or container CT imaging, etc.), the advantages are particularly obvious.

BRIEF DESCRIPTION OF THE DRAWINGS

A brief introduction will be given below for the drawings to be used in the description of the embodiments or related technologies. The present disclosure can be more clearly understood from the following detailed description with reference to the drawings.

It is obvious that the drawings illustrated as follows are merely some of the embodiments of the present disclosure. Those skilled in the art could obtain other drawings from the accompanying drawings without any inventive efforts.

DETAILED DESCRIPTION OF THE INVENTION

The inventor has found that the related decomposition method based on fixed basis material combination has a good effect when the substance to be identified has a small range of atomic number variation, but a large decomposition error occurs when the range of atomic number variation is large. For example, attenuation coefficient functions of substance whose range of atomic number is from carbon (atomic number Z=6, representing organic matter) to lead (Z=82, representing a heavy metal) are quite different. If a fixed set of basis materials are used, for example, if carbon (Z=6) and tin (Z=50) are selected, the decomposition error of substances with Z>50 and near Z=28 in the scanned object is very large; if carbon (Z=6) and lead (Z=82) are selected, the decomposition error of substances with 30<Z<60 in the scanned object is very large; if tin (Z=50) and lead (Z=82) are selected, the decomposition error of substances with Z<50 in the scanned object is very large.

One technical problem to be solved by the present disclosure is to reduce a decomposition error caused by improper selection of the basis material combination.

The technical solutions in the embodiments of the present disclosure will be described in a clear and complete manner with reference to the accompanying drawings in the embodiments of the present disclosure.

Figure 1:
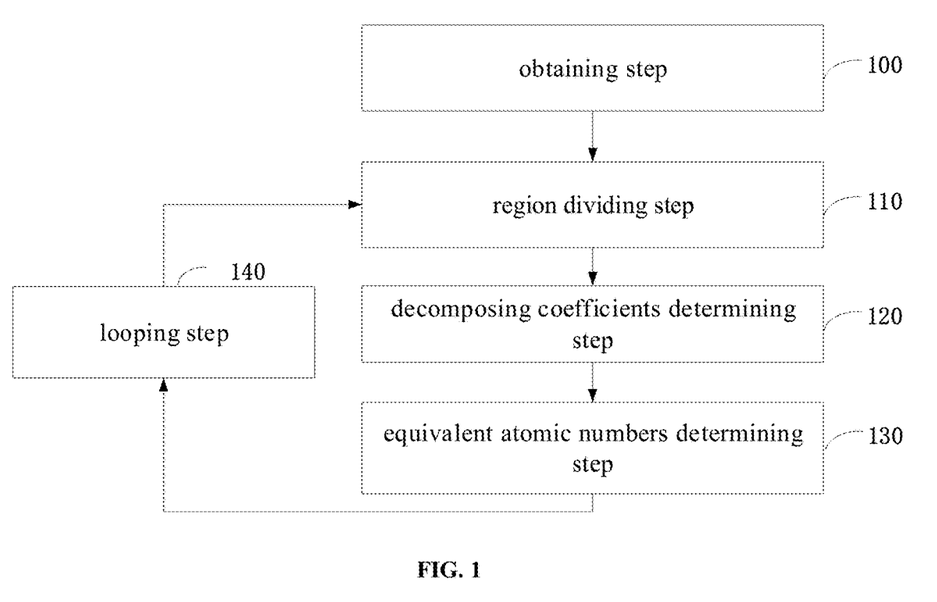
FIG. 1 is a flow diagram of one embodiment of a decomposition method based on basis material combination of the present disclosure.

FIG. 1 is a flow diagram of one embodiment of a decomposition method based on basis material combination of the present disclosure. As shown in FIG. 1, the method of this embodiment comprises steps 100~140.

In step 100 which can be called obtaining step, initial information such as decomposition coefficients and an equivalent atomic number of each point of a scanned object can be obtained.

The obtaining step obtains the decomposition coefficients and the equivalent atomic numbers of all points of the scanned object according to a fixed base material combination. That is the decomposition coefficients and the equivalent atomic numbers of all points of the scanned object can be determined according to the decomposition result based on a fixed basis material combination. The decomposition method based on the fixed basis material combination can be realized by referring to a decomposition method based on the fixed double basis materials in the prior art.

In step 110 which can be called region dividing step, the scanned object can be divided into a plurality of regions according to the equivalent atomic number of each point of the scanned object, wherein the basis material combinations used in each of the divided regions are different each other and one region adopts a same basis material combination.

The point is a pixel point or a voxel point. When the scanned object is not a single material, the scanned object is usually divided into a plurality of regions. If a processing speed of the computer is fast enough, each pixel or voxel point of the scanned object can be divided into one region at most. If a processing speed of the computer is limited, a plurality of points in the scanned object whose difference of equivalent atomic number is less than a preset range can be divided into one region.

In step 120 which can be called decomposing coefficients determining step or a decomposing step, with respect to each of the divided regions, decomposition coefficients of each point in the region can be determined based on the basis material combination used in the region.

In step 130 which can be called equivalent atomic numbers determining step, in the case where the change on decomposition coefficient based on the decomposition coefficients of all points in all the divided regions is not less than a preset threshold, with respect to each of the divided regions, equivalent atomic numbers for all points in the divided region can be re-determined based on the determined decomposition coefficients of all points in the divided region and atomic information of all basis materials of the basis material combination used in the divided region.

The atomic information includes, for example, atomic number and atomic weight.

In step 140 which can be called looping step, the region dividing step, the decomposing coefficients determining step and equivalent atomic numbers determining step can be cyclically performed according to the determined equivalent atomic numbers of each point of the scanned object until the change on decomposition coefficient based on the decomposition coefficients of all points in all the divided regions is less than a preset threshold, which means decomposition coefficients of the regions converge.

For example, if a change on decomposition coefficients of all points in a certain region is less than the preset threshold, the decomposition coefficients of the region is considered to converge.

Substance identification for each of divided region can be performed by using the equivalent atomic number of each point in each region after convergence. In the case where the change on decomposition coefficients is less than the preset threshold, substance identification for each of divided region can be performed by using the equivalent atomic number of each point in the region.

In the above embodiment, a scanned object is divided into a plurality of regions, the basis material combinations used in each of the divided regions are different each other, and the scanned object is re-divided according to the re-determined equivalent atomic number of its each point until the change on decomposition coefficient meets certain conditions. Thereby, a decomposition method based on dynamic basis material combinations is realized, which reduces a decomposition error caused by improper selection of the basis material combination and improves the accuracy of the decomposition and substance identification of the multi-energy CT.

When the range of atomic number variation of the scanned object is large, such as medical CT enhanced imaging (which uses a contrast agent of a material such as iodine), high-energy or multi-energy CT imaging (such as security, air box or container CT imaging, etc.), the advantages are particularly obvious. And it has an important application value for clinical medical, security, industrial non-destructive testing and other fields.

The decomposition method based on basis material combination of the present disclosure is not only applicable to dual energy (energy spectrum) CT but also applicable to multi-energy CT if projection data of more energy spectrums can be acquired, such as three-energy CT data or energy spectrum CT data based on multi-energy photon counting detectors. In dual energy CT, each region uses a combination of double basis materials. In multi-energy CT, each region requires a combination of several basis materials of the same number as the energy spectrums. For example, in a three-energy CT, each region requires a combination of three basis materials. The specific equations of the subsequent embodiment are described by taking the dual-energy CT as an example. According to the decomposition method based on double basis materials of the dual-energy CT of the present disclosure, those skilled in the art can obtain the decomposition method of the multi-energy CT without any creative labor.

An exemplary implementation of step 120 is implemented by using an iterative method. The iterative method comprises: starting from t=1, calculating decomposition coefficients of each point in the region t based on a basis material combination of the region t, and then taking the decomposition coefficients of each point in the region t as known parameters for the next calculation, and calculating decomposition coefficients of each point in the region t+1 based on a basis material combination of the region t+1, and ending until t is increased to N, so as to obtain decomposition coefficients of each point in each region, wherein N represents number of regions.

The calculation method of the decomposition coefficients of each point in a certain region t based on a basis material combination of the region t comprises: calculating an integral of the decomposition coefficients of each point in the region along each path through which each ray passes according to projection data of the ray with various energies (such as projection data under high-energy and projection data under low-energy), an energy spectrum of the region, and attenuation coefficient functions corresponding to the basis material combination of the region; determining decomposition coefficients of each point in the region with a preset reconstruction algorithm according to the integral of the decomposition coefficients of each point in the region along each path through which each ray passes. The reconstruction algorithm can be, for example, a filtered back projection (FBP) algorithm.

The calculation method of the decomposition coefficients of each point in a certain region t based on a basis material combination of the region t is described by taking the combination of the double basis materials as an example in the present embodiment and can be specifically implemented by referring to Equations (1-10).

Assume that the scanned object is divided into N regions, expressed as:

$$\Omega_1, \Omega_2, \ldots, \Omega_N \quad (1)$$

Attenuation coefficient functions of the double basis materials used in each region are:

$$\mu_1(j,E), \mu_2(j,E), j=1,2,\ldots,N \quad (2)$$

Where j is the number of a different region.

The decomposition coefficients (or called as a decomposition coefficient image) of each point (pixel point or voxel point) based on double basis materials are recorded as:

$$b_1(x), b_2(x) \quad (3)$$

Where x represents a pixel point or a voxel point.

Then the projection data of X-ray with high (H)/low (L) energy in X-ray dual energy CT can be written as:

$$p_{L/H}(ray_i) = \int_0^{E_{max}^{L/H}} S_{L/H}(E) \exp\left(-\int_{ray_i}\left[\sum_{j=1}^{N} b_1^j(x)\mu_1(j,E) + b_2^j(x)\mu_2(j,E)\right]dl\right)dE \quad (4)$$

wherein, $$b_k^j(x) = \begin{cases} b_k(x), & x \in \Omega_j \\ 0, & x \notin \Omega_j \end{cases}, k=1,2 \quad (5)$$

$S_{L/H}(E)$ represents energy spectrum of ray source with high/low energy, $E_{max}^{L/H}$ represents a maximum energy of the energy spectrum of ray source with high/low energy, $ray_i$ represents a path through which the ith ray passes, and an integral of dl in Equation (4) is an integral of the relevant physical quantities along the path through which the ray passes.

"t" represents the currently solved region. Assume that the decomposition coefficient image of the regions other than region t are known. The decomposition coefficient image of the region t can be obtained by the foregoing decomposition method, it can be learned from the dual-energy projection Equation (4) that:

$$\begin{cases} p_L(ray_i) = \\ \int_0^{E_{max}^L} \check{S}_L(E)\exp\left(-\mu_1(t,E)\int_{ray_i} b_1(x,t)dl - \mu_2(t,E)\int_{ray_i} b_2(x,t)dl\right)dE \\ p_H(ray_i) = \\ \int_0^{E_{max}^H} \check{S}_H(E)\exp\left(-\mu_1(t,E)\int_{ray_i} b_1(x,t)dl - \mu_2(t,E)\int_{ray_i} b_2(x,t)dl\right)dE \end{cases} \quad (6)$$

wherein, $$\check{S}_{L/H}(E) = S_{L/H}(E)\exp\left(-\int_{ray_i}\left[\sum_{j=1,j\neq t}^{N} b_1^j(x)\mu_1(j,E) + b_2^j(x)\mu_2(j,E)\right]dl\right) \quad (7)$$

Since the decomposition coefficient images $b_1^j, b_2^j, j=1, 2, \ldots, N, j \neq t$ of the regions other than region t are known, and since $S_{L/H}(E)$ are also known, an energy spectrum of the region t $\tilde{S}_{L/H}(E)$ can be calculated, thereby an integral of the decomposition coefficient image of the region t along the path through which the ray $ray_i$ passes can be calculated by the dual-energy projection Equation (6), that is:

$$B_1(ray_i) = \int_{ray_i} b_1(x,t)dl, B_2(ray_i) = \int_{ray_i} b_2(x,t)dl \quad (8)$$

The decomposition coefficients of each pixel/voxel point can be reconstructed with a general CT reconstruction algorithm (such as FBP algorithm) according to the integral of the decomposition coefficient image of the region t along each path through which each ray passes, that is:

$$b_1(x,t) = \text{Recon}\{B_1(ray_i)|i\}, b_2(x,t) = \text{Recon}\{B_2(ray_i)|i\} \quad (9)$$

Where Recon represents a reconstruction algorithm.

Since it is limited to the region t, the final decomposition coefficient image is expressed as:

$$b_k(x) = \begin{cases} b_k(x,t), & x \in \Omega_t \\ b_k(x), & x \notin \Omega_t \end{cases}, k = 1, 2 \quad (10)$$

An exemplary method for determining an equivalent atomic number of each point in certain region in step 130 includes: determining an equivalent electron density of each point in a divided region according to a decomposition coefficient of each point in the region and an atomic number and atomic weight of all basis materials of the basis material combination of the region; determining an equivalent atomic number of each point in the region according to the decomposition coefficient and the equivalent electron density of each point in the region and the atomic number and atomic weight of all basis materials of the basis material combination of the region.

Taking the combination of double basis materials as an example, the calculating equations of the equivalent electron density $\rho_{eff}$ and equivalent atomic number $Z_{eff}$ of each point are as follows:

$$\rho_{eff}(x) = b_1(x)\frac{Z_1^j}{A_1^j} + b_2(x)\frac{Z_2^j}{A_2^j}, x \in \Omega_j \quad (11)$$

$$Z_{eff}(x) = \left[\left(b_1(x)\frac{(Z_1^j)^\alpha}{A_1^j} + b_2(x)\frac{(Z_2^j)^\alpha}{A_2^j}\right) / \rho_{eff}(x)\right]^{1/(\alpha-1)}, x \in \Omega_j$$

Where the atomic numbers of the double basis materials used in the region j are expressed as $Z_1^j$ and $Z_2^j$, and the atomic weights of the double basis materials are expressed as $A_1^j$ and $A_2^j$.

Where the parameter a is empirically set as follows:

$$\begin{cases} \alpha = 4.5, & \max(Z_1^j, Z_2^j) \leq 50 \\ \alpha = 2, & \max(Z_1^j, Z_2^j) > 50 \end{cases} \quad (12)$$

An exemplary region dividing method of the scanned object in step 110 includes: dividing all points located in a same subinterval of a predetermined atomic number relationship chain into one region according to a position of an equivalent atomic number of each point of the scanned object in the atomic number relationship chain, and materials corresponding to the atomic numbers on both endpoints of the subinterval is determined as basis materials constituting a basis material combination of the region.

A length (that is, the size of N in Equation 13) of the atomic number relationship chain is related to the accuracy of substance identification. The larger the length of the atomic number relationship chain, the more regions the object is divided into, the higher the accuracy of substance identification. As for the atomic numbers used to demarcate the boundary of the region in the atomic number relationship chain, for example, atomic numbers corresponding to common materials can be selected, or they can be set according to the materials contained in the detected object.

The equation for the foregoing region division method is expressed as follows:

$$6 = Z_0 < Z_1 < Z_2 < \ldots < Z_{N-1} < Z_N = 80$$

$$\Omega_j = \{x | Z_{j-1} \leq Z_{eff}(x) < Z_j\} \quad (13)$$

Where the double basis materials of the newly divided region can be selected as materials that $Z_1^j = Z_{j-1}$, $Z_2^j = Z_j$ corresponds to.

Figure 2:
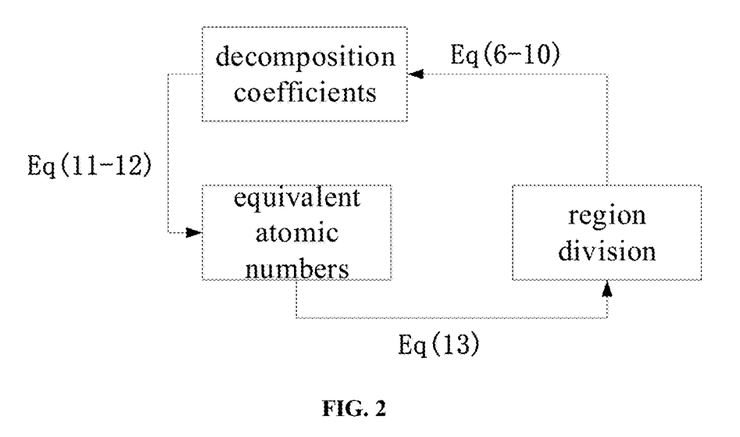
FIG. 2 is a flow diagram showing a cyclically executed decomposition method based on dynamic basis material combinations in which Equations (6-13) participate in the calculation.

As described above, a decomposition method based on dynamic basis material combinations of the present disclosure is cyclically performed before the decomposition coefficients of all regions converge. FIG. 2 is a flow diagram showing a cyclically executed decomposition method based on dynamic basis material combinations in which Equations (6-13) participate in the calculation, wherein Eq represents an equation, for example, Eq (10) represents Equation 10.

Figure 3:
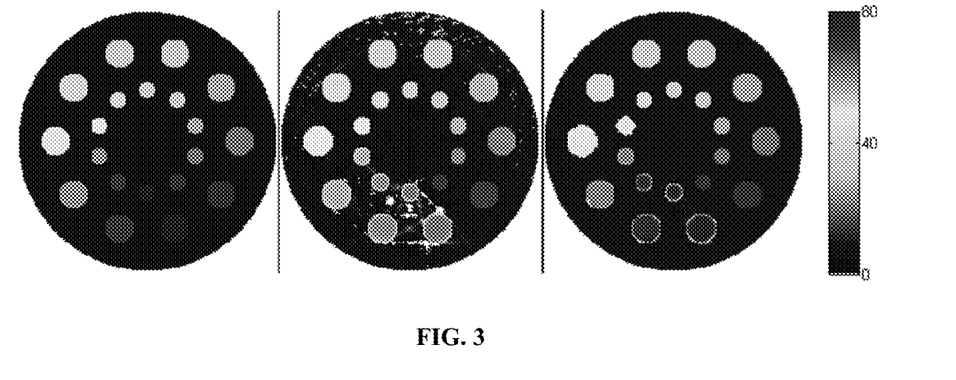
FIG. 3 shows a set of simulation experimental results.

FIG. 3 shows a set of simulation experimental results. The image size is 256*256, the pixel size is 1.6 mm*1.6 mm, the number of detector units is 736, the number of rotation angles is 540, and the rotation angle is 360°. The highest energy of the dual-energy CT ray source energy spectrum is 9 MeV and 6 MeV respectively. The material of the large cylinder in model is water, and the other small cylinders are divided into inner and outer groups. The inner and outer groups have the same materials, and the atomic numbers of the materials are: 13, 20, 26, 30, 34, 40, 50, 60, 70, 80 (counterclockwise rotation, color from shallow to deep). The three images in FIG. 3 from left to right in turn are: a real atomic number image, an atomic number image obtained by a traditional decomposition method based on fixed double basis materials, which uses materials with atomic numbers of 6 and 50 as fixed double basis materials, and an atomic number image obtained by the decomposition method based on dynamic basis material combinations of the present disclosure. It can be seen from the simulation results that the present disclosure can effectively improve the decomposition accuracy of the X-ray dual-energy CT, reduce decomposition error caused by an inconsistency of the materials between a dual-energy CT imaging model and the physical process, and has important significance and application value for improving the imaging quality and substance identification accuracy of dual-energy CT.

The present disclosure also proposes a decomposition apparatus based on basis material combination, comprising: One or more modules for performing the foregoing decomposition method.

Figure 4:
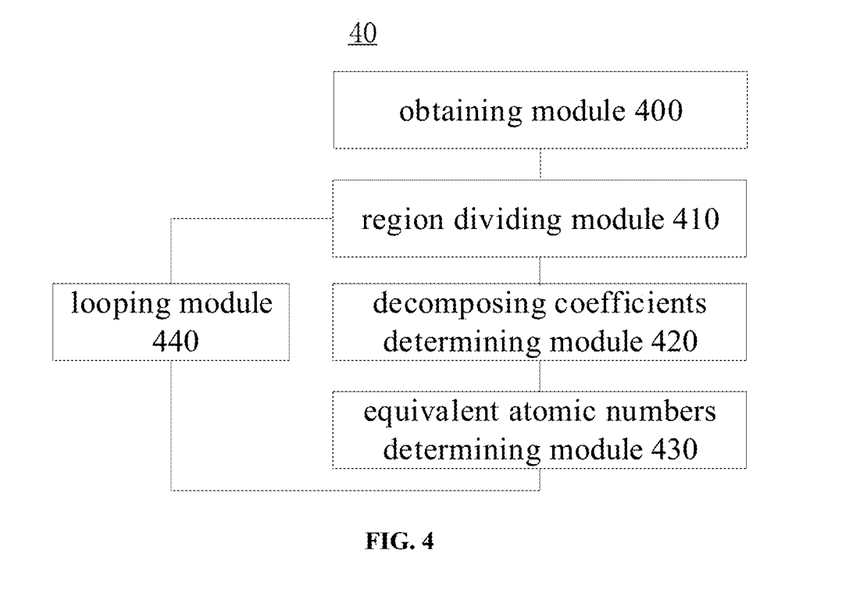
FIG. 4 is a schematic structural diagram of an embodiment of a decomposition apparatus based on basis material combination of the present disclosure.

FIG. 4 is a schematic structural diagram of an embodiment of a decomposition apparatus based on basis material combination according to the present disclosure.

As shown in FIG. 4, the decomposition apparatus based on basis material combination 40 includes: modules 400~440.

obtaining module 400 is configured for obtaining decomposition coefficients and an equivalent atomic number of each point of a scanned object.

region dividing module 410 is configured for dividing the scanned object into a plurality of regions according to the equivalent atomic number of each point of the scanned object, wherein the basis material combinations used in each of the divided regions are different each other.

decomposing coefficients determining module 420 is configured for, with respect to each of the divided regions, determining decomposition coefficients of each point in the region based on the basis material combination used in the region.

equivalent atomic numbers determining module 430 is configured for, with respect to each of the divided regions, determining equivalent atomic numbers for all points in the divided region based on the determined decomposition coefficients of all points in the divided region and atomic information of all basis materials of the basis material combination used in the divided region, in the case where the change on decomposition coefficient based on the decomposition coefficients of all points in all the divided regions is not less than a preset threshold.

looping module 440 is configured for looping the region dividing step, the decomposing coefficients determining step and equivalent atomic numbers determining step according to the determined equivalent atomic numbers of each point of the scanned object until the change on decomposition coefficient based on the decomposition coefficients of all points in all the divided regions is less than a preset threshold.

Optionally, obtains the decomposition coefficients and the equivalent atomic numbers of all points of the scanned object required at the beginning of the cycle are determined according to a preset (fixed) base material combination.

Optionally, the region dividing module 410 is configured for dividing all points located in a same subinterval of a predetermined atomic number relationship chain into one region according to a position of an equivalent atomic number of each point of the scanned object in the atomic number relationship chain, and materials corresponding to the atomic numbers on both endpoints of the subinterval is determined as basis materials constituting a basis material combination of the region.

Optionally, decomposing coefficients determining module 420 is configured for implementing by using an iterative method. The iterative method comprises: starting from t=1, calculating decomposition coefficients of each point in the region t based on a basis material combination of the region t, and then taking the decomposition coefficients of each point in the region t as known parameters for the next calculation, and calculating decomposition coefficients of each point in the region t+1 based on a basis material combination of the region t+1, and ending until t is increased to N, so as to obtain decomposition coefficients of each point in each region, wherein N represents number of regions.

Optionally, the calculation method of the decomposition coefficients of each point in a certain region t based on a basis material combination of the region t comprises: calculating an integral of the decomposition coefficients of each point in the region along each path through which each ray passes according to projection data of the ray with various energies (such as projection data under high-energy and projection data under low-energy), an energy spectrum of the region, and attenuation coefficient functions corresponding to the basis material combination of the region; determining decomposition coefficients of each point in the region with a preset reconstruction algorithm according to the integral of the decomposition coefficients of each point in the region along each path through which each ray passes. The reconstruction algorithm can be, for example, a filtered back projection (FBP) algorithm.

Optionally, the equivalent atomic numbers determining module 430 is configured for determining an equivalent electron density of each point in a divided region according to a decomposition coefficient of each point in the region and an atomic number and atomic weight of all basis materials of the basis material combination of the region, and for determining an equivalent atomic number of each point in the region according to the decomposition coefficient and the equivalent electron density of each point in the region and the atomic number and atomic weight of all basis materials of the basis material combination of the region.

Figure 5:
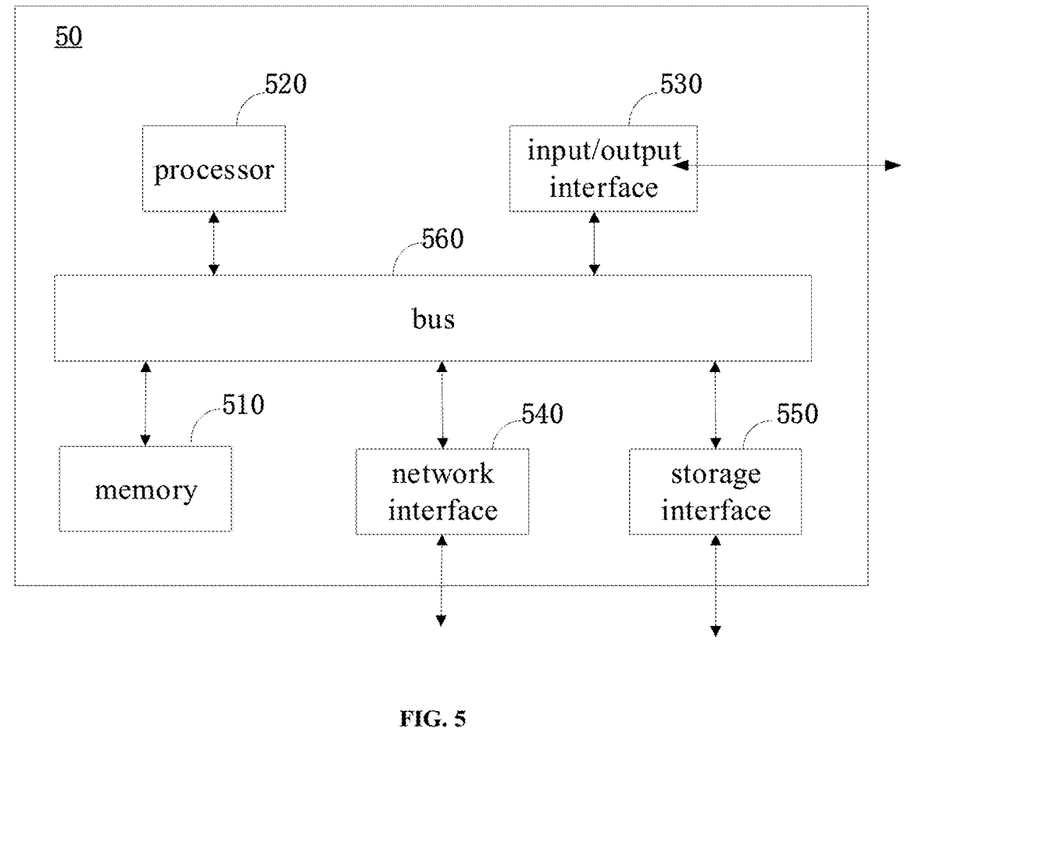
FIG. 5 is a schematic structural diagram of still another embodiment of the decomposition apparatus based on basis material combination of the present disclosure.

FIG. 5 is a schematic structural diagram of still another embodiment of the decomposition apparatus based on basis material combination of the present disclosure.

As shown in FIG. 5, the decomposition apparatus based on basis material combination 50 includes a memory 510 and a processor 520 coupled to the memory 510. The processor 520 is configured to perform the decomposition method in any of the foregoing embodiments based on the instructions stored in the memory 510.

The memory 510 may include, for example, a system memory, a fixed non-volatile storage medium, or the like. The system memory stores, for example, an operating system, an application, a boot loader, and other programs.

The apparatus 50 may also include an input/output interface 530, a network interface 540, a storage interface 550, and the like. These interfaces 530, 540, 550, the memory 510 and the processor 520 can be connected, for example, via a bus 560. The input/output interface 530 provides a connection interface for input/output devices such as a display, a mouse, a keyboard, and a touch screen. The network interface 540 provides a connection interface for various networked devices. The storage interface 550 provides a connection interface for external storage devices such as SD cards and USB flash drives.

The present disclosure also provides a computer readable storage medium storing a computer program, the program being executed by a processor to implement the decomposition method of any of the foregoing embodiments.

It shall be understood by those skilled in the art that embodiments of the present disclosure can be provided as a method, a system, or a computer program product. Accordingly, the present disclosure may take the form of an entirely hardware embodiment, an entirely software embodiment, or an embodiment combining both software and hardware. Moreover, the present disclosure may take the form of a computer program product implemented on one or more computer-usable non-transitory storage media (including but not limited to disk storage, CD-ROM, optical storage, etc.) having computer usable program code contained therein.

The above are only some of the embodiments of the present disclosure and are not intended to limit the present disclosure. Any modification, equivalent substitution, improvement, etc. within the spirit and principles of the present disclosure should be covered in the scope of protection of the present disclosure.

What is claimed is:

1. A decomposition method based on basis material combination, comprising:

obtaining step for obtaining decomposition coefficients and an equivalent atomic number of each point of a scanned object;

region dividing step for dividing the scanned object into a plurality of regions according to the equivalent atomic number of each point of the scanned object, wherein the basis material combinations used in each of the divided regions are different each other;

decomposing coefficients determining step for, with respect to each of the divided regions, determining decomposition coefficients of each point in the region based on the basis material combination used in the region;

equivalent atomic numbers determining step for, with respect to each of the divided regions, determining equivalent atomic numbers for all points in the divided region based on the determined decomposition coefficients of all points in the divided region and atomic information of all basis materials of the basis material combination used in the divided region, in the case where the change on decomposition coefficient based on the decomposition coefficients of all points in all the divided regions is not less than a preset threshold; and looping step for looping the region dividing step, the decomposing coefficients determining step and equivalent atomic numbers determining step according to the determined equivalent atomic numbers of each point of the scanned object until the change on decomposition coefficient based on the decomposition coefficients of all points in all the divided regions is less than a preset threshold.

2. The method according to claim 1, wherein said region dividing step comprises:

dividing all points located in a same subinterval of a predetermined atomic number relationship chain into one region according to a position of an equivalent atomic number of each point of the scanned object in the atomic number relationship chain, and materials corresponding to the atomic numbers on both endpoints of the subinterval is determined as basis materials constituting a basis material combination of the region.

3. The method according to claim 1, wherein said decomposition coefficients determining step comprising: for each of the divided regions, calculating an integral of the decomposition coefficients of each point in the region along each path through which each ray passes according to projection data of the ray with various energies, an energy spectrum of the region, and attenuation coefficient functions corresponding to the basis material combination of the region;

determining decomposition coefficients of each point in the region according to the integral of the decomposition coefficients of each point in the region along each path through which each ray passes.

4. The method according to claim 3, wherein the energy spectrum of a region is determined according to an energy spectrum of ray source, the decomposition coefficients of all points in other regions outside the region, and the attenuation coefficient functions corresponding to the basis material combinations of the other regions.

5. The method according to claim 1, wherein said equivalent atomic number determining step comprises:

determining an equivalent electron density of each point in a divided region according to a decomposition coefficient of each point in the region and an atomic number and atomic weight of all basis materials of the basis material combination of the region;

determining an equivalent atomic number of each point in the region according to the decomposition coefficient and the equivalent electron density of each point in the region and the atomic number and atomic weight of all basis materials of the basis material combination of the region.

6. The method according to claim 1, wherein the obtaining step obtains the decomposition coefficients and the equivalent atomic numbers of all points of the scanned object according to a preset base material combination.

7. The method according to claim 1, further comprising:

in the case where the change on decomposition coefficients is less than the preset threshold, performing substance identification for each of divided region by using the equivalent atomic number of each point in the region.

8. The method according to claim 1, wherein the point comprises a pixel point or a voxel point.

9. A decomposition apparatus based on basis material combination, comprising:

a memory; and a processor coupled to the memory, the processor being configured to perform the method of claim 1 based on instructions stored in the memory.

10. A non-transitory computer readable storage medium storing a computer program, the program being executed by a processor to implement the method of claim 1.

* * * * *